Sept. 29, 1936. P DOT Plant Pat. 197
ROSE
Filed March 16, 1936
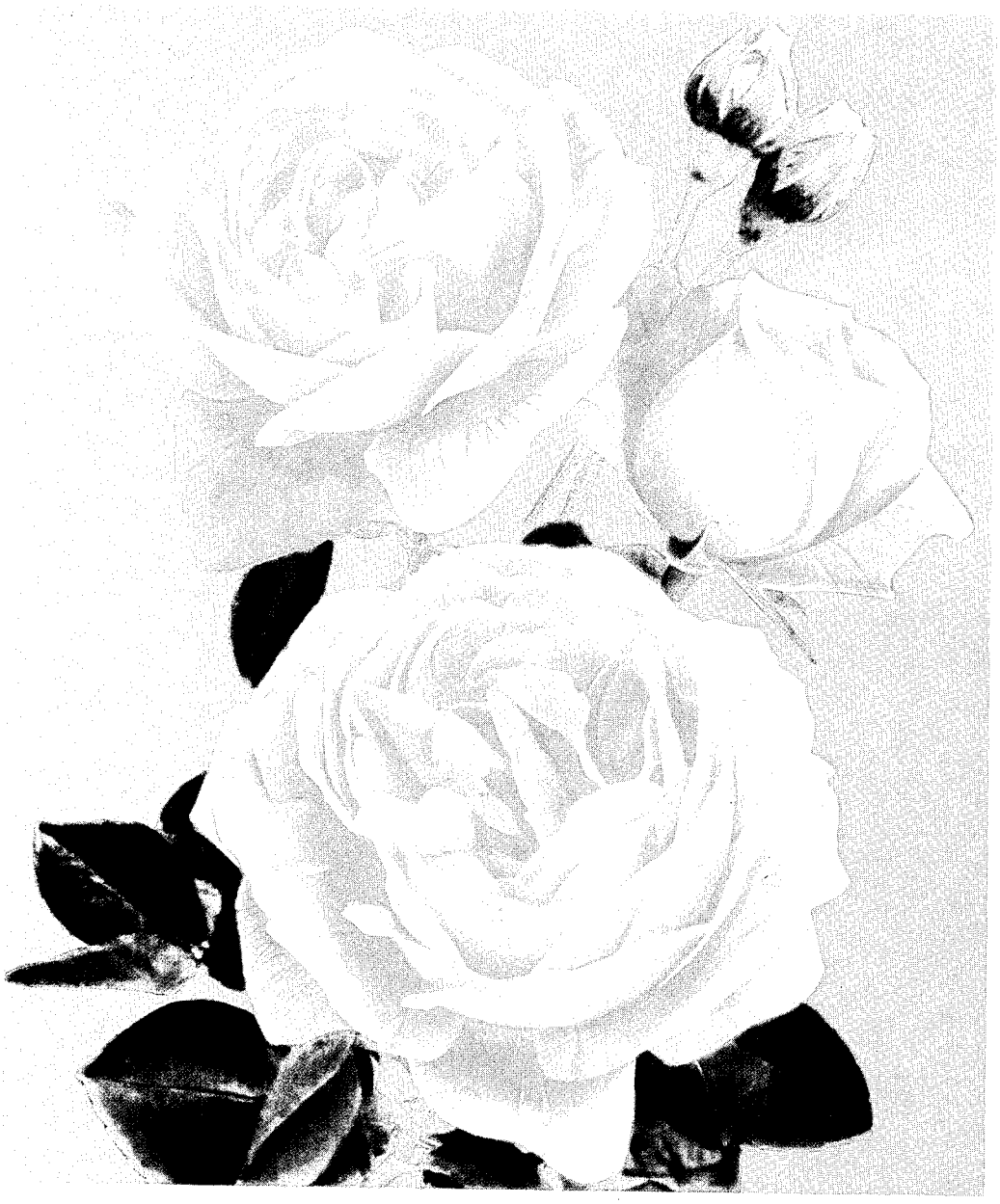
Inventor
Pedro Dot
By Robert Robb
Attorney Patented Sept. 29, 1936

Plant Pat. 197

UNITED STATES PATENT OFFICE

197

ROSE

Pedro Dot, St. Feliu de Llobregat, Spain, assignor to The Conard-Pyle Company, West Grove, Pa.

Application March 16, 1936, Serial No. 69,186

1 Claim. (Cl. 47—61)

The present discovery relates to a new and distinct variety of rose plant, originating as a sport of the hybrid pernetiana rose "Condesa de Sastago."

The novelty of this new rose resides primarily in the coloring effect of the bloom produced by the peculiar arrangement of the color of the petals which compose each bloom. This coloring effect has never been found heretofore in the hybrid pernetiana family.

As is well known, the parent of the present variety is a Spanish novelty, a double rose combining, when full blown, more or less consistently the brilliant coloring of copper and yellow—fiery copper on the inside of the petals and rich gold on the reverse, a most interesting and popular color contrast.

As distinguished from this, however, the bloom of my new rose presents a basic color of light cadmium, some of the flowers having stripes or blotches of carmine on one or more petals while others have half a petal carmine and/or a whole petal of that color. In still others of the flowers half of the complete bloom will be carmine, and rarely can two flowers be found alike.

These colors, as the blooms age, change and by virtue of this variegation of the various blooms en masse, a vivid distinctiveness in this type of roses is presented not found in the parent or anywhere else in roses to my knowledge.

Asexual reproduction of the plant has shown that the novel characteristic referred to is permanent.

The following is a detailed description of this new variety, all references to color being based on the Ridgway's color chart as regards the description of the color of the blossoms or buds, and dictionary terms being used as to fruit, foliage, wood and thorns:

Parentage:
Sport of Condesa de Sastago.

Classification:
Hybrid pernetiana.

*Flower*

Blooming habit:
Continuous.

Bud:
*Size.*—Large.
*Form.*—Ovoid, pointed.
*Color*—Pale yellow with carmine markings.
*Sepals.*—Some branched, some not, foliate ends. Stand out straight.
*Calyx.*—Wide and deep, shallow goblet shaped, smooth, apple fragrance when rubbed.
*Peduncle.*—Short, strong, yellowish light green, covered with setae.
*Opening.*—Opens well, does not ball.

Bloom:
*Size.*—4 to 4½ inches.
*Borne.*—Singly.
*Stems.*—Medium length, strong.
*Form.*—Open, loose form, a few petaloids fold over the stamens on most flowers.
*Permanence.*—Lasts well.
*Petalage.*—40 to 50.
*Color.*—Various, the basic color is light cadmium, some flowers have stripes or blotches of carmine on one or more petals, others have half a petal carmine, others a whole petal will be carmine. Rarely can two flowers be found alike, as the bloom ages the carmine changes to deep rose-pink and the cadmium of the reverse to pale lemon yellow.

Petals:
*Texture.*—Heavy leathery.
*Appearance.*—Metallic.
*Form.*—Pear shaped.
*Arrangement.*—Loosely formed.
*Persistence.*—Drop off cleanly.
*Fragrance.*—Strong fruity fragrance.
*Lasting quality.*—Lasts until petals fall.

Genital organs:
*Stamens, anthers.*—Average number. Color—orange. Arrangement—uneven.
*Stamens, filaments (threads).*—Various lengths. Color—yellow.
*Pollen.*—Orange.
*Styles.*—Bunched uneven length, a trifle shorter than stamens.
*Stigmas.*—Pale yellow.
*Ovaries.*—Normal.

Fruit:
Variety fertile with own pollen.
*Form.*—Globular.
*Aspect.*—Normal.
*Color at maturity.*—Orange to nasturtium.
*Sepals.*—Fold back against the stem.

*Plant*

Form:
Bush.

Growth:
Upright, vigorous, branching.

Foliage:
*Number leaflets to compound leaf.*—Some 3, some 5, some 7.
*Size.*—Medium.
*Quantity.*—Abundant.
*Color.*—New foliage—bronzy light green, edges deep bronze. Mature foliage—upper side, dark green, under side, medium green.

*Shape.*—Ovoid, pointed.

*Texture.*—Heavy leathery.

*Edge.*—Serrated.

*Serration.*—Shallow, uneven.

*Ribs and veins.*—Ordinary, well marked but not deeply impressed.

*Rachis.*—Color—green. Under side—prickly.

*Stipules.*—Medium, medium width, pointed, serrated.

*Disease resistance.*—Subject to black spot.

Wood:

*New wood.*—Green.

*Old wood.*—Green.

Thorns:

*Quantity.*—Numerous.

*Form.*—Slightly hooked, broad base with tip opposite base of thorn.

*Color when young.*—Pale green.

*Position.*—Irregular.

*Prickles.*—None.

*Short needles.*—None.

I claim:

The new and distinct variety of Rose plant, as shown and described, characterized by the ever-changing variegated coloring of its fragrant flowers through all stages of their development producing a new color effect in hybrid perneti-ana roses.

PEDRO DOT.